United States Patent [19]

Cheronis et al.

[11] Patent Number: 5,573,916
[45] Date of Patent: Nov. 12, 1996

[54] IMMUNOGENIC CONSTRUCTS COMPRISING B-CELL AND T-CELL EPITOPES ON COMMON CARRIER

[75] Inventors: John C. Cheronis, Lakewood; Claire Coeshott, Denver, both of Colo.

[73] Assignee: Coretech, Inc., Denver, Colo.

[21] Appl. No.: 246,278

[22] Filed: May 19, 1994

[51] Int. Cl.$^6$ .............................. G01N 33/53; C07K 1/00; A61K 39/12; A61K 39/21
[52] U.S. Cl. ...................... 435/7.1; 530/350; 424/204.1; 424/208.1
[58] Field of Search ............................. 424/208.1, 204.1; 435/7.1; 530/350; 436/513

[56] References Cited

U.S. PATENT DOCUMENTS

| | | | |
|---|---|---|---|
| 5,229,490 | 7/1993 | Tam | 530/324 |
| 5,276,013 | 1/1994 | Conrad et al. | 514/2 |

FOREIGN PATENT DOCUMENTS 0429816  6/1991  European Pat. Off. ........ C07K 17/02

OTHER PUBLICATIONS

Webster's Ninth New Collegiate Dictionary, 1990, p. 602.
Lehner, et al, 1989, "Immunogenicity of synthetic peptides . . . ," J. Immunol. 143(8):2699–2705.
Brown, 1993, "Aids Vaccine Trials . . . ," The Wash. Post Newspaper, Jun. 10, 1993.
Cohen, 1993, "Jitters Jeopardize AIDS . . . ," Science 262;980–981.
Butini, et al, "Comparative Analysis of . . . ," J. Cell. Biochem., Suppl. 18B, Abstract J306, p. 147.
Schild, et al, 1990, "Human Immunodeficiency Virus and AIDS . . . ," The Lancet 335:1081–1084.
Valmori et al, "Use of Human Universally Antigenic Tetanus Toxin T Cell Epitopes as Carriers for Human Vaccination," The Journal of Immunology, vol. 149, No. 2, Jul. 15, 1992, pp. 717–721.

Primary Examiner—Lynette F. Smith
Attorney, Agent, or Firm—Schwegman, Lundberg, Woessner & Kluth, P.A.

[57] ABSTRACT

The present invention relates to immunogenic constructs capable of eliciting an IgG antibody response in a host in the absence of adjuvant.

10 Claims, 10 Drawing Sheets

IMMUNOGENIC CONSTRUCTS COMPRISING B-CELL AND T-CELL EPITOPES ON COMMON CARRIER

BACKGROUND OF THE INVENTION

The present invention relates to inherently immunogenic constructs capable of eliciting an IgG, IgE or IgA antibody response in a host in the absence of adjuvant.

In an effort to prevent disease in a host caused by pathogens, the host body's immune system attempts to destroy the pathogen itself and neutralize its products. This strategy underlies the field of vaccination, which is based on two key elements of adaptive immunity: specificity and memory. Specificity increases a vaccine's effectiveness whereas memory cells allow the immune system to mount a stronger response in reaction to a second encounter with antigen. This secondary response is both faster to appear and more effective than the primary response.

The response to most antigens depends on both T cells and B cells recognizing that antigen. This type of antigen is called T-dependent. Antigen entering the body is processed by antigen presenting cells (APC) and presented to T helper cells. Antigen is recognized by B cells as well. The T cells deliver help to the these B cells which are consequently stimulated to differentiate and divide into antibody-forming cells.

A number of antigens are, however, capable of activating B cells without, or in the virtual absence of, T-cell help. These antigens are referred to as T-independent antigens. The immune response to T-dependent and T-independent antigens is qualitatively different. For example, the secondary response to T-independent antigens resembles the primary response. Such a secondary response to T-independent antigens usually does not exceed the primary response in magnitude and is almost entirely confined to IgM antibody production. In contrast, the secondary IgG antibody response to T-dependent antigens is far stronger and appears earlier. It seems therefore that T-independent antigens do not usually induce memory and maturation of the response as characterized by class switching to IgG antibodies and an increase in affinity of antibodies for antigen. Therefore, vaccines which do not elicit T cell help for B cells are of limited value.

In a response to a T-dependent antigen, it has been found that distinct sites on the antigen (epitope, hapten or antigenic determinant) are recognized by T and B cells, thus, these sites may be termed T-cell and B-cell epitopes, respectively. The vast majority of soluble T-dependent antigens elicit only low level antibody responses unless they are administered with an adjuvant, a substance which non-specifically enhances the immune response to an antigen. However, the use of adjuvants may be associated with several disadvantages: they are often toxic, they may skew the antibody repertoire to certain isotypes which may have different effector functions from those produced in the absence of adjuvants and they may alter the nature of the antigen so that epitopes other than those recognized in the native antigen become immunodominant. In addition, due to their size, many T-dependent antigens are non-immunogenic even in the presence of an adjuvant eg. synthetic peptides.

To overcome the disadvantages and to optimize the advantages of T-dependent antigens, various vaccines have been designed based on conjugates combining B and T cell epitopes. However, in many cases either low level production of antibodies was elicited, multiple immunizations were required, infants failed to mount a secondary response, or the conjugate required the presence of an adjuvant in order to elicit any response.

Therefore, a clear need exists for a vaccine capable of inducing the production of memory cells and of eliciting a specific immune response to pathogenic invaders.

SUMMARY OF THE INVENTION

The present invention provides an immunogenic construct comprising a carrier with at least one type of B-cell epitope and at least one type of T-cell epitope attached to the carrier at distinct attachment sites. The construct is capable of inducing IgG antibody production to the B-cell epitope without the addition of adjuvant.

The present invention also provides a method for co-arraying B cell or T cell epitopes from different antigens providing a multipurpose vaccine.

The invention also provides a method of eliciting an IgG response to a B-cell epitope in a mammal whereby an immunogenic amount of the construct is administered to the host mammal.

The present invention also provides a method of assessing whether an epitope is recognized by T cells.

Figure 7:
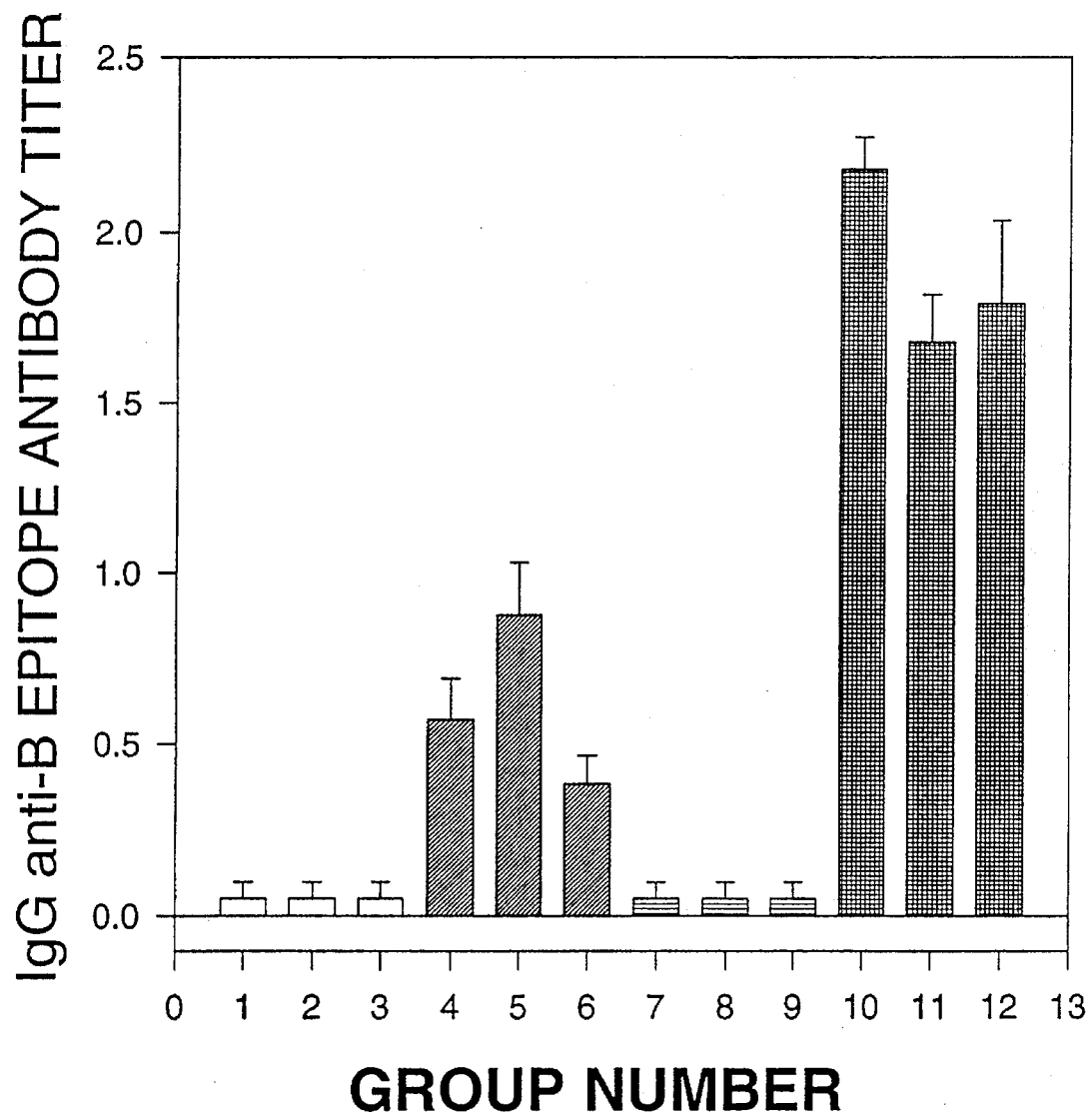
FIG. 7—Illustrates levels of IgG anti-B cell epitope antibodies produced in Balb\c female mice in response to secondary intraperitoneal administration of various doses of a co-array of a *Plasmodium berghei* B cell epitope and cOA 323–339 on dex$_{500}$ and various doses of an array of only the B epitope on dex$_{500}$. In both FIGS. 7 and 8, the following defines the groups depicted.
Figure 8:
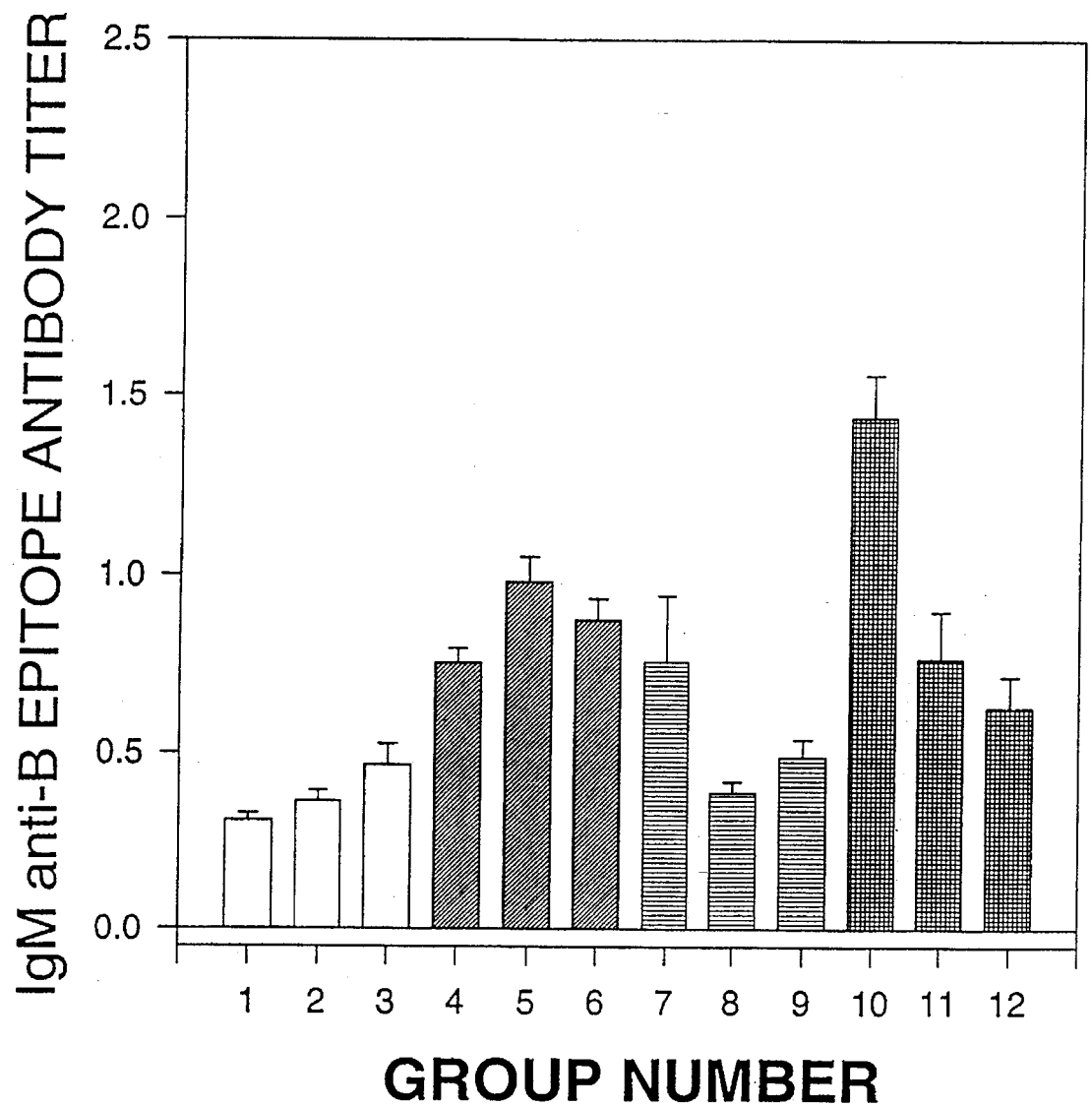

| KEY TO FIGS. 7 AND 8 | | |
|---|---|---|
| GROUP | ADJUVANT | DOSE (ug) |
| 1. B epitope dex$_{500}$ | NO | 500 |
| 2. B epitope dex$_{500}$ | NO | 50 |
| 3. B epitope dex$_{500}$ | NO | 5 |
| 4. (B + T) epitope dex$_{500}$ | NO | 500 |
| 5. (B + T) epitope dex$_{500}$ | NO | 50 |
| 6. (B + T) epitope dex$_{500}$ | NO | 5 |
| 7. B epitope dex$_{500}$ | Al(OH)$_3$ | 500 |
| 8. B epitope dex$_{500}$ | Al(OH)$_3$ | 50 |
| 9. B epitope dex$_{500}$ | Al(OH)$_3$ | 5 |
| 10. (B + T) epitope dex$_{500}$ | Al(OH)$_3$ | 500 |
| 11. (B + T) epitope dex$_{500}$ | Al(OH)$_3$ | 50 |
| 12. (B + T) epitope dex$_{500}$ | Al(OH)$_3$ | 5 |

FIG. 8—Illustrates levels of IgM anti-B cell epitope antibodies produced in Balb\c female mice in response to secondary administration of various doses of a co-array of a *Plasmodium berghei* B cell epitope and cOA 323–339 on dex$_{500}$ and various doses of an array of only the B epitope on dex$_{500}$.

Figure 9:
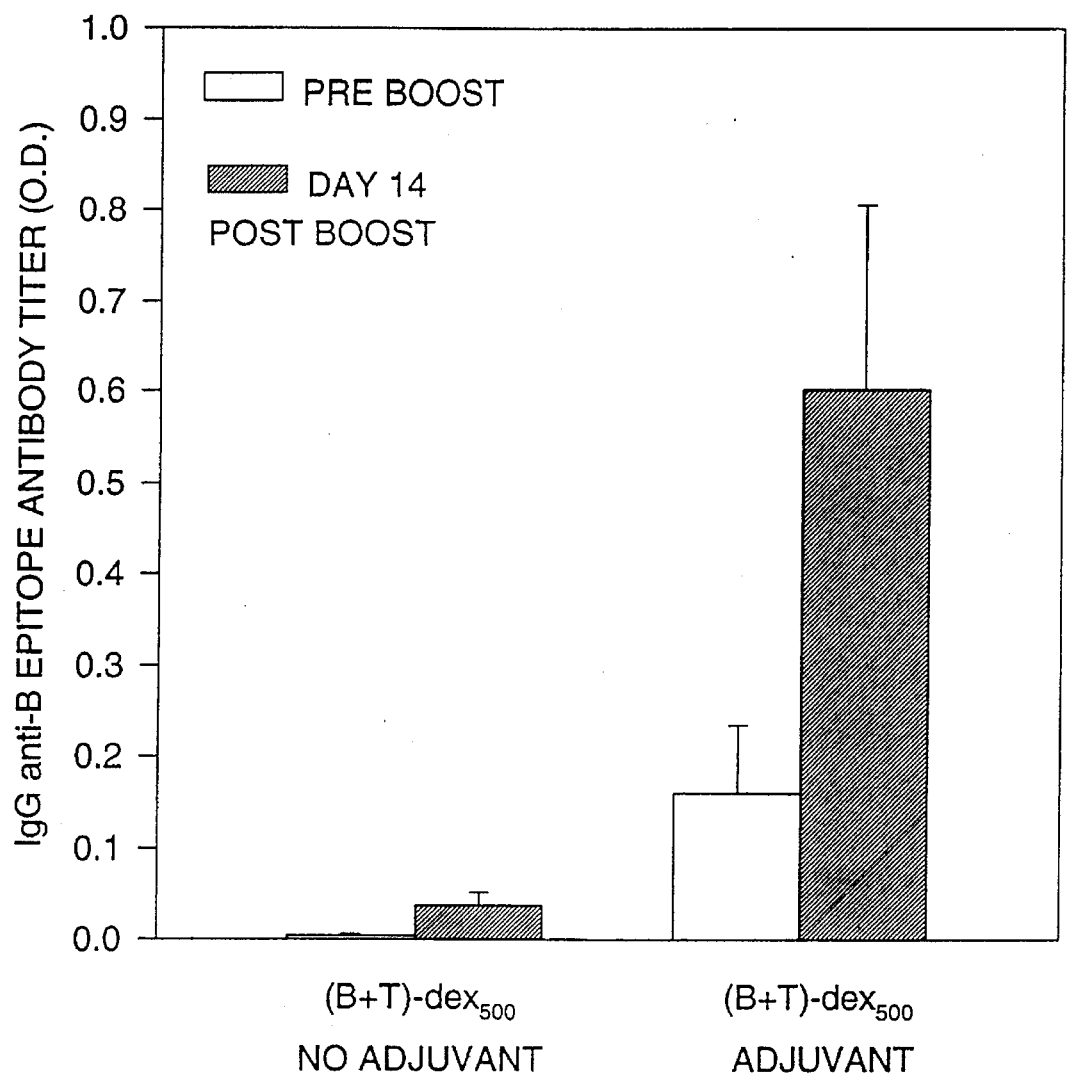

FIG. 9 shows levels of IgG anti-HIV epitope antibodies.

Figure 10:
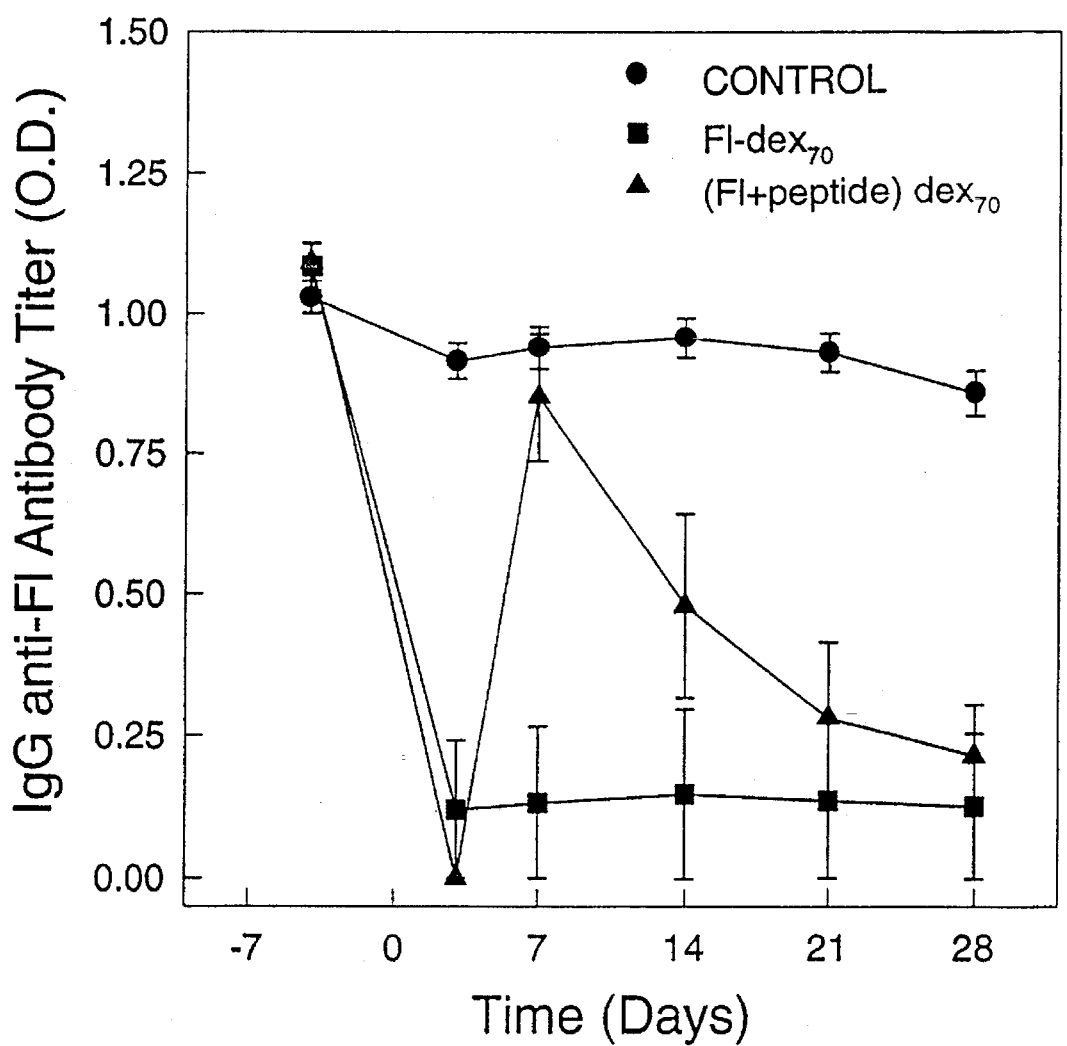

FIG. 10—Illustrates levels of IgG anti-Fl antibodies obtained in immune Balb\c female mice after treatment with either Fl-dex$_{70}$ or a co-array of Fl and cOA 323–339 on dex$_{70}$.

DETAILED DESCRIPTION OF THE INVENTION

The present invention relates to constructs capable of inducing IgG or IgA or IgE antibody production to a B-cell epitope. The constructs comprised of at least one molecule of the B-cell epitope and at least one molecule of the T-cell epitope attached to a carrier at distinct attachment sites.

As used herein, "B-cell epitope" refers to any antigen, hapten, epitope or antigenic determinant which is recognized by B-cell immunoglobulin receptors and is capable of eliciting the production of antibodies with appropriate help from T cells when administered to an animal. A B-cell epitope includes T-dependent and T-independent antigens.

As used herein, "T-cell epitope" refers to any antigen, hapten, epitope or antigenic determinant which is recognized by T-cells.

These epitopes may consist of or be derived from, but are not limited to, bacteria, rickettsiae, fungi, viruses, parasites, drugs or chemicals. They may include, for example, small molecules such as peptides, saccharides, oligosaccharides, toxins, endotoxins, and the like.

As used herein, "immunostimulatory amount" refers to that amount of vaccine that is able to stimulate the immune response of the recipient for the prevention, amelioration, or treatment of diseases.

The immune system is the primary biological defense of the host against potentially pernicious agents. These pernicious agents may be pathogens, such as bacteria or viruses, as well as modified self cells, including virus-infected cells, tumor cells or other abnormal cells of the host. Collectively, these targets of the immune system are referred to as antigens. The recognition of antigen by the immune system rapidly mobilizes immune mechanisms to destroy that antigen, thus preserving the sanctity of the host environment.

It is believed that antigen entering a host body interacts initially with T and B cells along two separate but parallel pathways. In order to be recognized by helper T cells, antigen is first picked up and processed by cells known as antigen-presenting cells (APC). These APC subsequently present the antigen in a highly recognizable form to the T helper cells. In the case of a protein antigen, processing degrades the antigen intracellularly to a series of linear peptides which the T cells can recognize. As a consequence of recognition, the T cells become activated.

In contrast, B cells can recognize antigen directly without the need for prior processing and can become activated as a consequence of recognition. Activated T cells then help the B cells both to divide and differentiate into antibody-secreting cells and to differentiate into memory B cells which will mount the response to secondary challenge with antigen producing IgG (or IgA or IgE) antibodies. These interactions are referred to as collaboration between the T cells and B cells and results in IgG (or IgE or IgA) antibody production in the primary response.

It is postulated that two types of signal are required to activate a B cell. These include antigen interacting with B cell immunoglobulin receptors and a stimulating signal or signals from T cells. The present invention is based on the premise that optimal stimulatory response to any antigen involves both interactions. In this way memory cells are activated and highly specific antibodies are produced.

It has been determined that for a given hapten and carrier, there exists a threshold number and spacing of haptens on a polymer carrier (or the like) which are essential to form a cluster of connected antigen receptors to stimulate IgM antibody formation (Dintzis et al., Proc. Nat'l. Acad. Sci. USA, 73:10; 3671–3675 (1976); Dintzis et al., J.Immunol., 143:4; 1239–1244 (1989), incorporated herein by reference). These studies indicate the existence of a sharp threshold in the immunogenic response elicited by various polymer preparations. In particular, all polymers with less than 12 to 16 appropriately-spaced hapten groups per molecule were nonimmunogenic (i.e., no immune response was induced), while those polymers with greater than this number were fully immunogenic. The results indicated that the immunological response at its most elementary level is quantized. In other words, a minimum specific number of antigen receptors (approximately 12 to 16 for the work reported) must be connected together as a spatially continuous cluster (termed, an immunon by Dintzis) before an immunogenic signal is delivered to the responding B cell.

In addition, it was determined that immunogenicity is directly related to the molecular mass of the carrier as well as the hapten valence. All linear polymers tested which had an effective hapten valence greater than 20 and a molecular mass larger than 100,000 Da were immunogenic. In contrast, polymers with a molecular mass of less than 100,000 Da were not only non-immunogenic but also were suppressive inasmuch as they could specifically prevent an immune response to the larger molecules bearing the same hapten. It was concluded that the physical characteristics of the molecule rather than the specific chemical characteristics of the carrier, act as primary determinants in the ability of a soluble haptenated-polymer to activate an anti-hapten immune response.

The application of the above described theory has been limited to homogenous receptor conjugates wherein multiple copies of identical epitopes have been arrayed on a polymer backbone. Activation was limited to B cells and the concomitant production of IgM antibodies.

According to the present invention, a controlled number of B cell epitopes and T cell epitopes are conjugated to inert carriers of high molecular weight (>100,000 Da). By "controlled" it is meant that the number and spacing of B epitopes must be sufficient to deliver an immunogenic signal to the responding B cell. In a preferred embodiment, the number of B cell epitopes conjugated to the carrier is at least about 20. In co-arraying B-cell and T-cell epitopes, an inherently immunogenic conjugate is created which does not require the addition of adjuvant in order to elicit an antibody response although it may be desirable, in some circumstances, to add adjuvant in order to enhance the response or to protect certain epitopes from degradation in in vivo applications.

For application to the vaccine field, as well as for research application, these epitopes may be synthetic linear peptides, small organic molecules (haptens), nucleic acids, oligonucleotides or lipids.

The applicants have determined that adjuvant may enhance the apparent half-life of the presently claimed conjugate. However, for the conjugates to be inherently immunogenic (i.e., whereby IgG antibodies are produced in the absence of adjuvant) it is preferred that epitopes are used which are stable. In a more preferred embodiment, the epitopes have a half-life in plasma of at least about 1 hour.

According to the present invention, the carrier may be any naturally-occurring, semisynthetic or entirely synthetic molecule of various molecular weights. The chemical composition of the carrier does not affect the immunogenicity of the construct. In a preferred embodiment, polymeric carriers are chosen from dextran, carboxymethyl cellulose, agarose, ficoll, polyacrylamide, and polyvinyl alcohol.

The specific conjugation method used may vary depending upon the nature of the specific epitopes used and the type of carrier chosen. Representative techniques are described herein for the conjugation of epitope to a dextran backbone.

The invention also describes a means for changing the quality of the immune response inasmuch as the presence of the T cell epitope can switch the antibody response to the B cell epitope from an IgM antibody response to an IgG antibody response and additionally elicit the induction of immunological memory and affinity maturation.

Because adjuvants can alter epitope conformation, the ability to use an immunogenic construct without the use of an adjuvant, and therefore without alteration of the conformation in the epitope of interest, may allow the induction of a qualitatively different immune response.

The inherently immunogenic constructs may also be used for the derivation of antibodies of therapeutic or diagnostic value.

The addition of multiple epitopes (all B or all T or a mixture) also allows the preparation of "one shot" vaccines. Thus, if different epitopes exist on different strains of the same organism or if they exist at different stages of the life cycle of an organism, then the presently described technology may be used to vaccinate against all of these various strains or stages at one time.

Because the conjugates prepared according to the present invention are able to cause a switch in antibody class and induce the production of memory cells, the constructs containing co-arrays of B and T cell epitopes have great potential as vaccines. For application to the vaccine field, co-arrays are prepared using an epitope defined as a T cell epitope in humans (or animals) and a B cell epitope from a known pathogen, e.g., the NANP repeat sequence [(NANP)$_n$] from the circumsporozoite protein of the human malarial parasite, *Plasmodium falciparum* (Dame et al., *Science* 225:593 (1984)). For vaccine use in humans, a T cell epitope from, for example, tetanus toxoid could be used that is known to be recognized universally by humans regardless of HLA type (Panina-Bordignon et al., *Eur.J.Immunol.* 19:2237 (1989)). Alternatively, epitopes such as PPd or malaria Cs.T3 may be used.

Thus, in another embodiment, the invention includes methods of preparing a vaccine against malaria and also the human immunodeficiency virus (HIV).

To prepare a vaccine against HIV, the "universal" T cell epitope from tetanus toxoid is co-arrayed with the principal neutralizing determinant from the gp120 envelope protein of HIV. Any widely recognized T cell epitope could be used in these co-arrays.

Pharmaceutically acceptable vehicles are well known in the art. They include, for example, sterile liquids, such as water and oils, including those of petroleum, animal, vegetable or synthetic origin, such as peanut, soybean, mineral oils and the like. Saline solutions and aqueous dextrose and glycerol solutions can also be employed as liquid carriers.

The invention also provides a method of eliciting an IgG response to a B-cell epitope in a host whereby an immunogenic amount of the construct is administered to the host mammal.

The invention also relates to the treatment of a recipient by administration of an immunostimulatory amount of the vaccine. "Recipient" refers to any subject for whom the treatment may be beneficial and includes mammals, particularly humans, and other animals, such as chickens. The vaccine of the invention may be administered by any route, but is preferably administered by intravenous, intramuscular, or subcutaneous injections.

In a further embodiment, these constructs may be used as research tools to assess whether a structure (or moiety) functions as a T or B cell epitope. For example, dextran of high molecular weight (e.g., 500,000 Da) is conjugated with a small hapten such as fluorescein (Fl) at a known density while some reactive groups are left accessible for the attachment of a putative T cell epitope. Once the T epitope under investigation is attached, the final construct is injected into a host. The production of an IgG anti-hapten response and the development of memory, which is measured by the production of an IgG response after secondary challenge exceeding the magnitude of the primary response, would indicate that the epitope was one which induced T helper cells to collaborate with B cells.

In a reciprocal manner, a construct bearing a known, potent, stable T cell epitope is prepared and this product is used to raise an IgG antibody response to various epitopes of choice. In this way, the invention also provides a method of producing a diagnostic and/or research reagent to detect agents that are characteristic of diseases caused by, for example, bacteria, viruses, fungi, parasites or chemicals by immunizing a host with a vaccine described herein so that the host produces antibodies (or B cells) against the agents. Once isolated, the antibodies may be used to make up a diagnostic reagent to detect agents that are characteristic of the disease.

The following examples are intended to illustrate but not limit the invention.

EXAMPLES

Example 1

Preparation of Peptides

Peptides were synthesized by solid-phase peptide synthesis using an automated peptide synthesizer (Milligen/Biosearch, Novato, Calif. or Applied Biosystems, Inc., Foster City, Calif.) (Barany et al., *The Peptides: Analysis, Synthesis, Biology;* Gross, E., Meienhofer, J., Eds.; Academic Press: New York, Vol.2; pp 1–284. (1980)). N-tert-Butyloxycarbonyl protection was employed for all peptide syntheses, and finished peptides were cleaved from the synthesis resin using standard HF cleavage procedures (Stewart, et al., Laboratory Techniques in Solid-Phase Peptide Synthesis. In *Solid-Phase Peptide Synthesis,* 2nd ed.; Pierce Chemical Company: Rockford, Ill., pp 85–88. (1984))

Free peptides were extracted from the resin, purified by preparative reversed-phase high performance liquid chromatography (HPLC), and lyophilized. Amino acid compositional analysis of purified peptides was carried out via the Waters PICO-TAG chemistry following 22–24-hour vapor-phase hydrolysis with constantly boiling 6M HCl (Bidlingmeyer, et al., *J. Chromatogr.* 336:93–104 (1984)). Amino acid analyses were within ±5% of the values predicted by the respective peptide sequence.

Example 2

Maleimidation of Dexamine$_{500K}$ and Subsequent Peptide Conjugation

Dexamine$_{500K}$ was acylated with a five-fold molar excess (relative to total amine content) of gamma maleimido n-butyric acid N-hydroxysuccinimide ester in HEPES buffer (0.2M, pH 8). The resulting gamma maleimido n-butyryl-dexamine$_{500K}$ (GMB-dexamine$_{500K}$) was purified by repetitive ultrafiltration using PBS as the buffer medium. Subsequent peptide conjugation was accomplished by addition of the desired cysteine-containing peptide(s) to the GMB-dexamine$_{500K}$. Conjugation reactions were terminated by the addition of excess mercaptoethanol. Peptide-containing dextran conjugates were purified by repetitive ultrafiltration using PBS as the buffer medium. Lyophilization afforded the conjugates as fluffy, white powders. Assessment of peptide substitution density was made by PICO-TAG amino acid analysis (Bidlingmeyer, et al., *J. Chromatogr.* 336:93–104 (1984)).

Example 3

Fluoresceination/Maleimidation of Dexamine$_{500K}$ and Subsequent Peptide Conjugation Dexamine$_{500K}$ was acylated with 0.3 equivalents (relative to total amine content) of fluorescein isothiocyanate (FITC) in carbonate buffer (0.2M, pH 9). The resulting fluorescein-containing dexamine$_{500K}$ (Fl-dexamine$_{500K}$) was purified by repetitive ultrafiltration using PBS as the buffer medium, acylated with a five-fold molar excess (relative to total amine content) of gamma maleimido n-butyric acid N-hydroxysuccinimide ester, and purified by size exclusion chromatography on Sephadex G-25 resin using PBS as the eluent. Subsequent conjugation was accomplished by addition of either the desired cysteine-containing peptide (=CI-0104, the ovalbumin peptide), then mercaptoethanol or by addition of mercaptoethanol alone. Fluorescein/peptide-containing dextran conjugates were purified by dialysis using PBS as the buffer medium. Lyophilization afforded the conjugates as fluffy, orange powders. Assessment of fluorescein and peptide substitution density were made by PICO-TAG amino acid analysis (Bidlingmeyer, et al., *J. Chromatogr.* 336:93–104 (1984)).

Example 4

Response to T-independent Antigen

Small organic molecules (haptens) arrayed on inert backbones of high molecular weight (e.g., Dextran>100,00 Da) are, as previously described, immunogenic and can induce a hapten-specific IgM antibody response when injected into mice or when added to spleen cell cultures (Dintzis et al. 1989), indicating that this response occurs in the virtual absence of help from T cells (a T-independent response). IgG3 is also variably produced; this isotype is also known to be produced in a T-independent fashion. The data that follow relate to such constructs.

Figure 1:
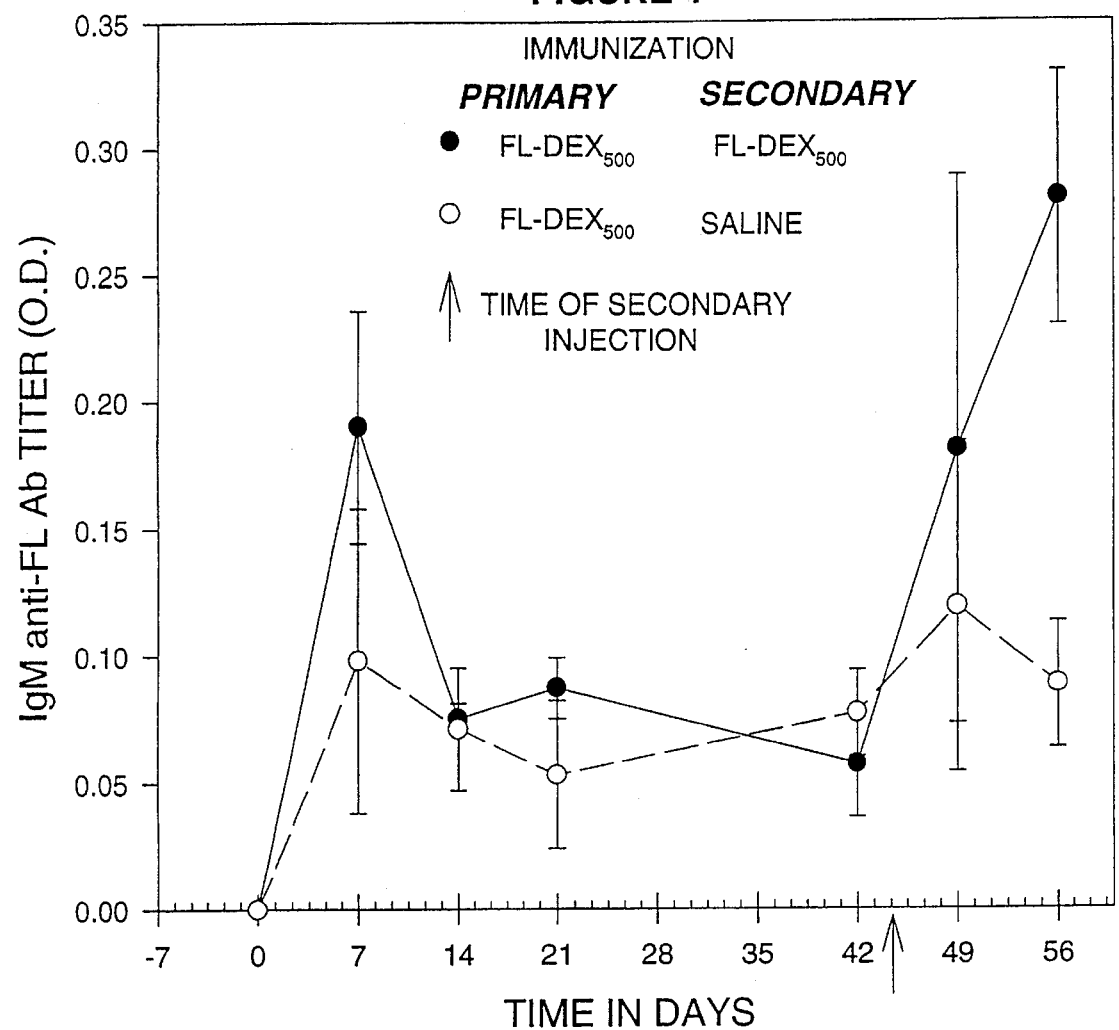
FIG. 1—Illustrates levels of IgM anti-Fl antibodies produced in Balb\c female mice in response to primary and secondary intraperitoneal administrations of 100 ug Fl-dex$_{500}$.
Figure 2:
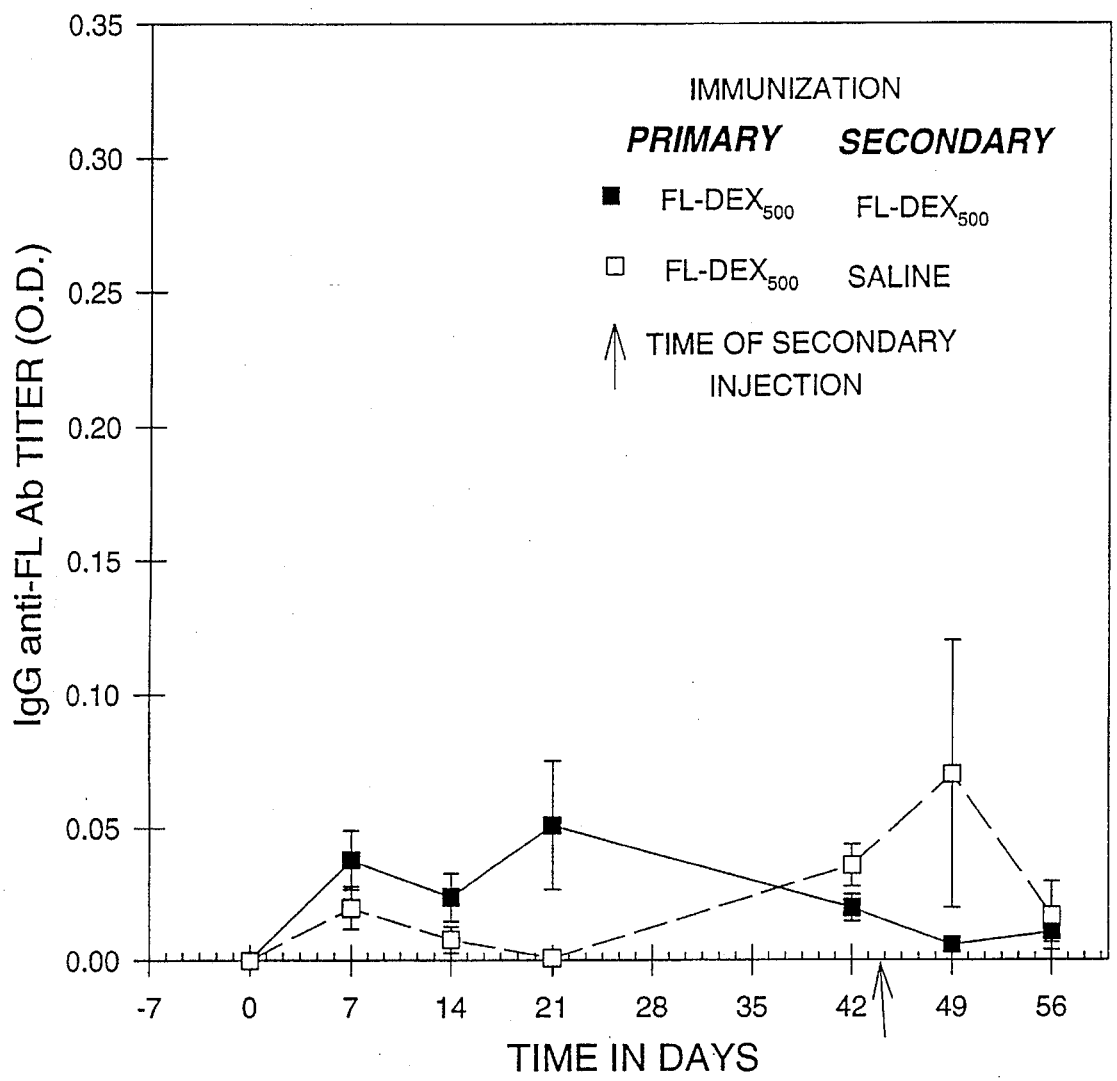
FIG. 2—Illustrates levels of IgG anti-Fl antibodies produced in Balb\c female mice in response to primary and secondary intraperitoneal administrations of 100 ug Fl-dex$_{500}$.

When Balb\c female mice were injected with the small hapten, fluorescein (Fl), conjugated to dextran of 500,000 MW (referred to as Fl-dex$_{500}$) at a substitution ratio of 40 copies of Fl per dextran molecule, IgM but not IgG antibody responses peaked within 7 days and persisted at low levels for at least 6 weeks (FIGS. 1 and 2). Specifically, groups of mice (n=8) were immunized intraperitoneally (ip) with either 100 ug Fl-dex$_{500}$ or saline and sera were obtained at various times thereafter. Forty five days later, mice received either a second injection of 10 ug of the construct or of saline. Sera were obtained 4 and 11 days after this second injection. Levels of IgM and IgG anti-Fl antibodies in the sera were assayed by ELISA using gelatin conjugated with Fl at a low substitution density to coat the microtiter plates.

The ELISA was performed as follows: Microtiter plates (Immunolon II, Dynatech Laboratories, Alexandria, Va.) were coated overnight at 4° C. with Fl-gelatin at 0.1 ug/well. After blocking non-specific sites on the wells with PBS/gelatin, various dilutions of sera were added and the plates were incubated at room temperature for 2 hours. Plates were then washed and antibody binding was detected with horseradish peroxidase-conjugated isotype-specific antibodies (Kirkegaard and Perry Laboratories, Gaithersburg, Md.) followed by the ABTS ($2_1$ $_2^1$-azino-bis (3-ethylbenzthiazoline-6-sulfonic acid)) substrate. Data are expressed as OD405 nm of the ABTS product.

In the situation where a second dose of Fl-dex$_{500}$ was administered to these mice, an IgG response again did not develop and the IgM once again developed but did not greatly exceed the magnitude of the initial response (FIGS. 1 and 2). Therefore, it appears that this antigen did not cause the induction of memory B cells which would have given rise to a secondary response consisting of IgG antibodies.

It should be mentioned that IgG antibodies could be detected in animals receiving Fl-dex$_{500}$ if the assays were set up in certain ways, i.e., using a densely-substituted Fl-gelatin as a readout antigen in ELISA together with low dilutions of sera. The subclass distribution of the IgG in the primary response was found to be IgG1 and IgG3 only, with no contribution from IgG2a or IgG2b (data not shown). IgG3 is known to be produced in a T cell-independent fashion perhaps induced as a result of cytokine production by non-T cells (Snapper et al. *J. Exp. Med.* 175:1367 (1992)). The explanation for the presence of IgG1 is not readily apparent. However, it is possible that environmental stimulation of the mice has occurred by some unknown T-dependent antigen which has raised antibodies cross-reactive with Fl.

However, the data for this example were generated using a Fl-gelatin with very low substitution density to overcome the problem of low affinity, non-specific antibody binding. In addition, the sera were more highly diluted. Thus, under these conditions, IgG was only detectable in animals receiving constructs bearing the T cell epitope.

Example 5

Response to T-independent Ag/T-cell Epitope Co-array

To determine whether the presence of a T cell epitope in a co-array with Fl could switch the antibody response to IgG with concomitant development of memory, Fl and molecules of a synthetic peptide were co-conjugated to the same dextran molecule ($dex_{500}$). The peptide chosen was a tryptic product of chicken ovalbumin (cOA), consisting of residues 323–339, which is well-documented in the literature as a potent T cell epitope in mice (Shimonkevitz et al. *J. Immunol.* 133:2067 (1984)). This synthetic peptide was conjugated via an additional cysteine residue on its N terminus to the dextran backbone. The substitution density of Fl was once again 40 copies\dextran molecule whereas that of the T epitope was 150 copies\dextran molecule.

Groups of Balb\c female mice (n=8) were immunized ip either with 100 ug of Fl-$dex_{500}$ or with 100 ug of a co-array of Fl and 323–339 on $dex_{500}$ ([Fl+peptide]-$dex_{500}$) and sera were taken at various times thereafter. Forty five days after primary injection, the groups were further divided so that half was boosted with the same dose of the immunizing construct whereas the other half received only saline. Sera were obtained 4 and 11 days later and assayed for anti-Fl antibodies as described in Example 4.

Figure 3:
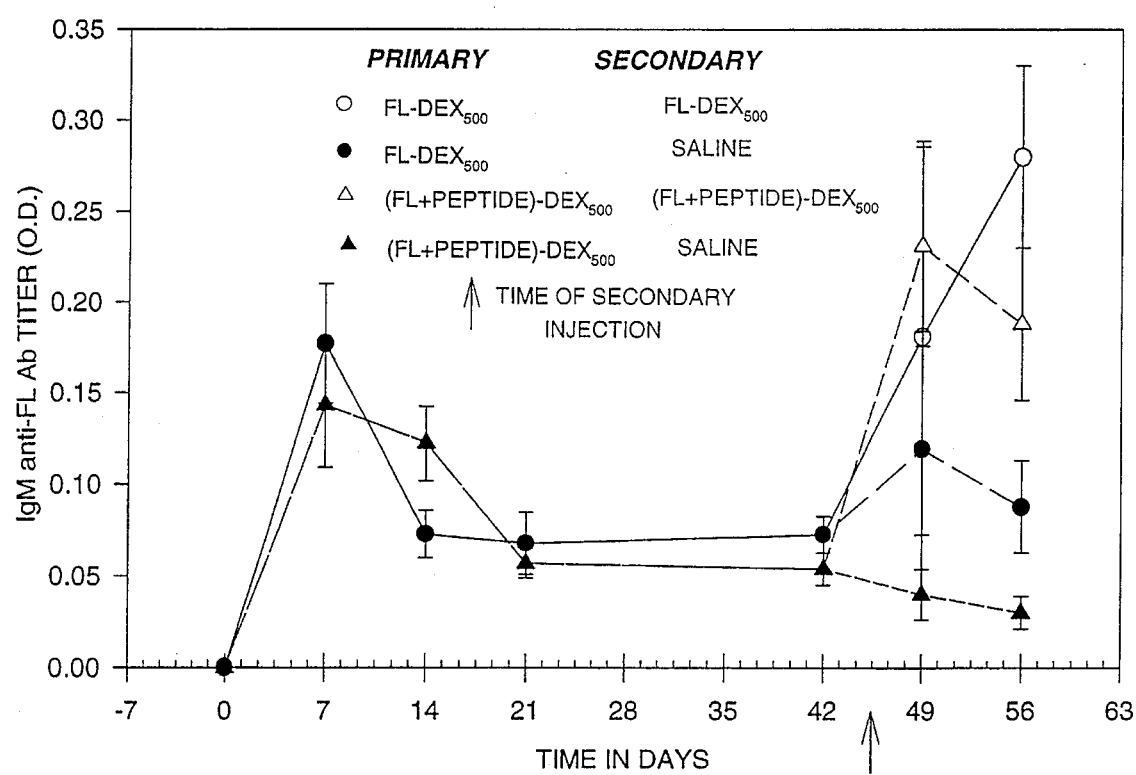
FIG. 3—Illustrates levels of IgM anti-Fl antibodies produced in Balb\c female mice in response to primary and secondary intraperitoneal administrations of either 100 ug Fl-dex$_{500}$ or 100 ug of a co-array of Fl and cOA 323–339 on dex$_{500}$.
Figure 4:
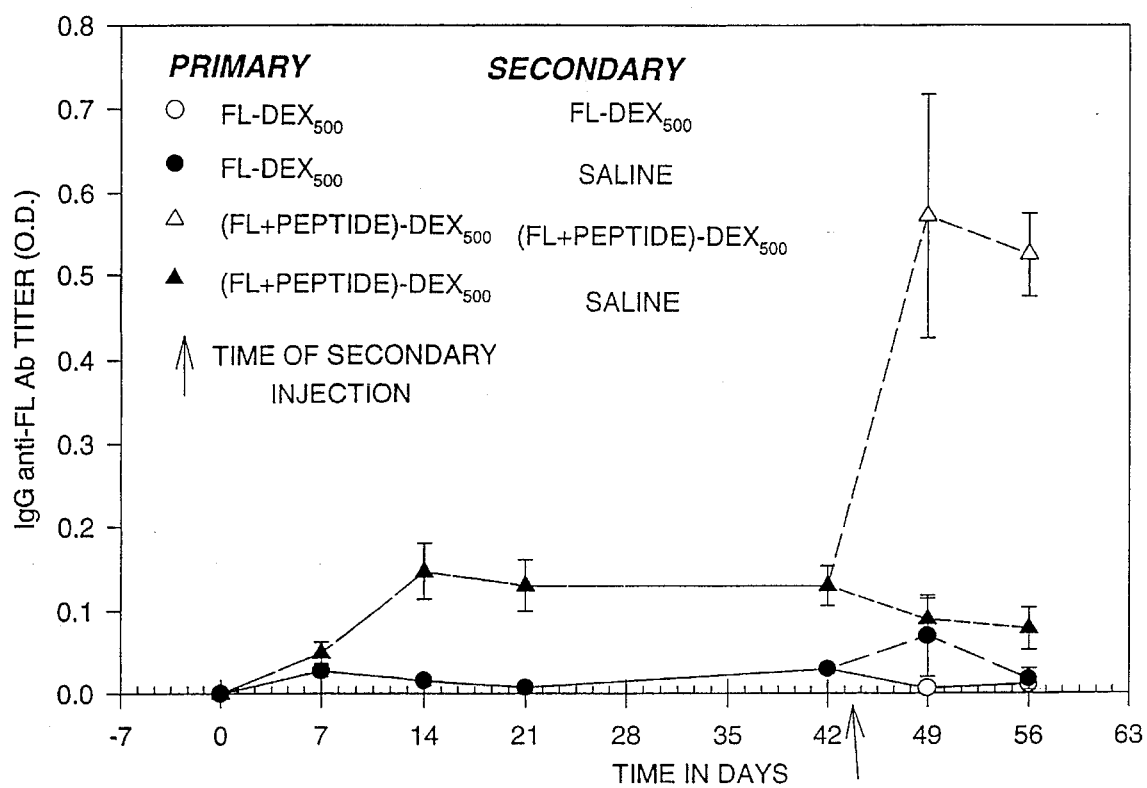
FIG. 4—Illustrates levels of IgG anti-Fl antibodies produced in Balb\c female mice in response to primary and secondary intraperitoneal administrations of either 100 ug Fl-dex$_{500}$ or 100 ug of a co-array of Fl and cOA 323–339 on dex$_{500}$.

Mice injected with [Fl+peptide]-$dex_{500}$ developed IgG anti-Fl antibody titres which plateaued at approximately 14 days and remained at this level for at least 6 weeks (FIGS. 3 and 4). IgM and IgG antibodies were also raised to the ovalbumin peptide itself (data not shown).

Mice receiving a second dose of [Fl+peptide]-$dex_{500}$ exhibited a typical secondary antibody response producing a rapid IgG anti-Fl response which greatly exceeded the magnitude of the primary response (FIG. 4). These same mice also made IgM anti-Fl in response to this challenge but the response did not greatly exceed that of the primary response (FIG. 3). Mice receiving a second injection of Fl-$dex_{500}$ produced IgM (FIG. 3) but not IgG (FIG. 4) anti-Fl antibodies.

Thus, the addition of the T cell epitope to the hapten array has caused a switch in isotype from IgM to IgG and the secondary response has the hallmarks of a memory response. It is also assumed that the IgG antibodies in the secondary response would be of higher affinity than those produced in the primary response since affinity maturation would have taken place as a consequence of memory development.

Example 6

*Plasmodium falciparum*

To use an epitope that would have more relevance to the vaccine field, co-arrays were prepared using a B cell epitope from a known pathogen, the NANP repeat sequence from the circumsporozoite protein of the human malarial parasite, *Plasmodium falciparum*. The T cell epitope was once again cOA 323–339.

The peptide comprising the B cell epitope had the following amino acid sequence: C(NANP)$_3$ and this was conjugated via the cysteine residue to $dex_{500}$. These two types of synthetic peptide were co-arrayed on $dex_{500}$. In addition, the B epitope was arrayed alone. The substitution densities on the co-array were 203 copies\dextran molecule and 273 copies\dextran molecule for the T and B epitopes respectively whereas that for B epitope when arrayed alone on dextran was 711 copies\dextran molecule.

Groups of Balb\c female mice (n=8) were either immunized ip with 100 ug of the co-array, referred to as (B+T)-$dex_{500}$, or with 100 ug of the B epitope arrayed alone on $dex_{500}$ (B-$dex_{500}$). Both types of construct were administered in PBS with or without 1 mg Al(OH)$_3$ as adjuvant. The doses were based on the weight of the dextran backbone.

Figure 5:
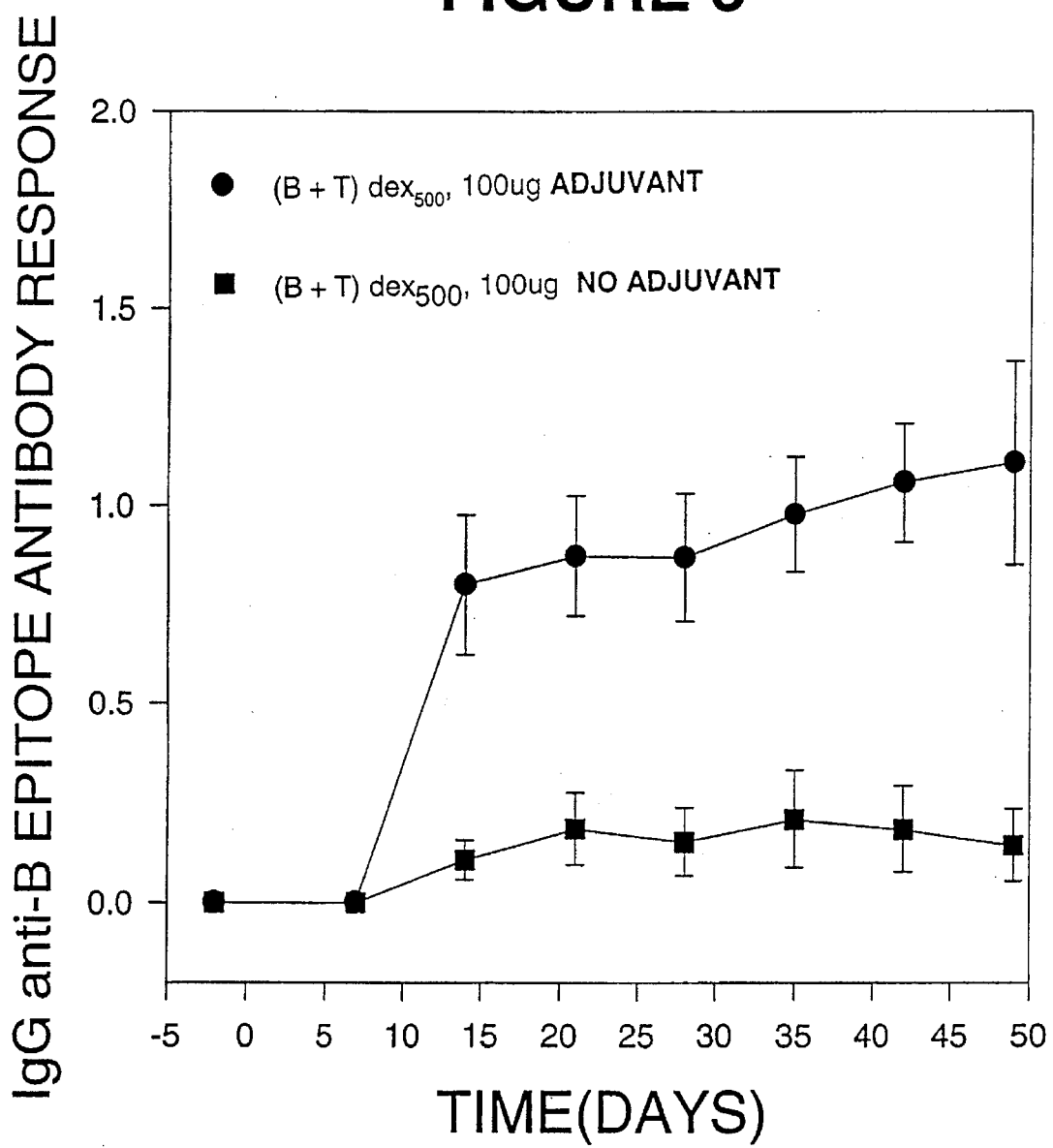
FIG. 5—Illustrates levels of IgG anti-NANP antibodies produced in Balb\c female mice in response to primary and secondary administrations of 100 ug of a co-array of a *Plasmodium falciparum* B cell epitope and cOA 323–339 on dex$_{500}$ in the presence and absence of Al(OH)$_3$.

Animals received a second injection of the same construct three weeks after the primary injection. Sera were obtained at various times and were assayed for the presence of IgG anti-NANP antibodies by ELISA using (NANP)$_3$-gelatin to coat the plates. After a single injection in the presence of adjuvant, mice receiving the co-array made IgG antibodies to the NANP sequence and the levels were increased after a second injection (FIG. 5). In the absence of adjuvant, however, only a very low IgG anti-NANP antibody response was detected which did not increase significantly after a boost (FIG. 5).

Figure 6:
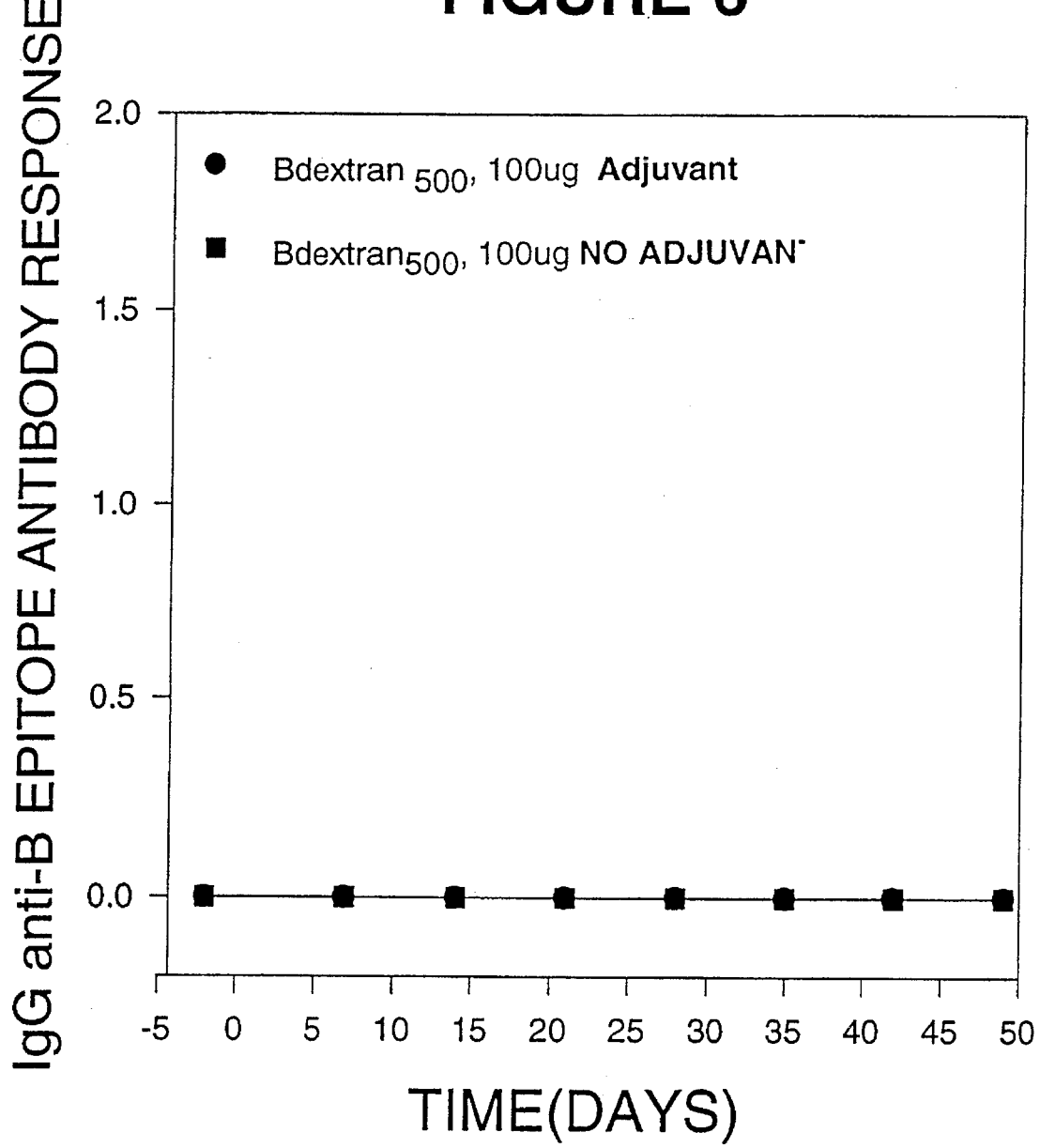
FIG. 6—Illustrates levels of IgG anti-NANP antibodies produced in Balb\c female mice in response to primary and secondary administrations of 100 ug of an array of a *P. falciparum* B epitope on dex$_{500}$ in the presence and absence of Al(OH)$_3$.

In mice receiving B-$dex_{500}$, with no T cell epitope co-arrayed, no IgG anti-NANP antibody response occurred even in the presence of adjuvant (FIG. 6). Therefore, once again, the T cell epitope is required to elicit an IgG antibody response to the arrayed B cell epitope.

Adjuvant is probably required to stabilize the NANP epitope against degrading petidases as the applicants have found that NANP has an extremely short half-life (less than 0.28 hr) in murine plasma.

Sera containing anti-NANP antibodies were tested in an infectivity assay for their ability to protect hepatocytes from infection by *P. falciparum*. A pool of sera was obtained from mice (n=8) that had been boosted three weeks previously with (B+T)-$dex_{500}$ in adjuvant. The pool had high IgG anti-NANP antibody activity. A pool of control sera was obtained from mice (n=8) that had been immunized with an irrelevant protein also in adjuvant.

Pooled sera at 1:100 dilution were subsequently tested in an in vitro infectivity assay. The control pool did not inhibit infection (100% infectivity) whereas the pool of sera from mice immunized with the co-array reduced infectivity to 11%.

Example 7

Co-arrays Without Adjuvant

In a similar situation to that described in Example 3, co-arrays were made on $dex_{500}$ of the T epitope, cOA 323–339, and a synthetic peptide representing a B cell epitope from *Plasmodium berghei* (the causative agent of murine malaria, Eichinger et al. (1986)). This peptide consists of the amino acid sequence: (DPPPPNPN)$_2$DGC which is conjugated via the cysteine residue to the dextran backbone. The substitution densities on the dex$_{500}$ were 126 copies and 323 copies of the T and B epitopes, respectively. The B-dex$_{500}$ was substituted with 351 copies of the B epitope per dextran molecule.

Groups of Balb\c female mice (n=8) were either immunized ip with 500, 50 or 5 ug of the co-array, referred to as (B+T)-dex$_{500}$ or were immunized ip with 500, 50 or 5 ug of the B epitope arrayed alone on dex$_{500}$ (B-dex$_{500}$). As in Example 3, both types of construct were administered in PBS with or without 1 mg Al(OH)$_3$ as adjuvant and the doses of construct were based on the weight of the dextran backbone. Animals received a second dose of the same construct five weeks later and sera were subsequently obtained two weeks later. Sera were assayed for IgG anti-B epitope antibodies by ELISA using gelatin conjugated with (DPPPPNPN)$_2$DGC to coat the plates.

Mice receiving B-dex$_{500}$ made no IgG antibodies to the berghei epitope (FIG. 7) although IgM antibodies were detected and adjuvant had no effect on the magnitude of these IgM responses (FIG. 8). However, mice receiving the co-arrays made good IgG antibody responses to the berghei epitope even in the absence of adjuvant (FIG. 7) although the magnitude of the response was increased in the presence of adjuvant (FIG. 7). IgM responses were also seen in mice receiving co-arrays (FIG. 8). It is likely that the ability of the berghei peptide to be immunogenic on a co-array in the absence of adjuvant is due to its inherent stability (measured as greater than 6 hours in murine plasma).

Example 8

HIV

Co-arrays were also made from the T cell epitope, cOA 323–339, and a B cell epitope from the envelope glycoprotein, gp120, of HIV. This epitope has been shown to be the principal neutralizing determinant (Rusche et al 1988) and it has also been described in the literature as a helper T cell epitope in mice (Takahashi et al. 1990). This peptide consists of the sequence:

C-amino caproic acid-NNTRKSIRIQRGPGRAFVTIGKIG and this was conjugated to dex$_{500}$ via the cysteine residue. The substitution densities on the dex$_{500}$ were 172 copies\dextran and 203 copies\dextran for the T and B epitopes respectively whereas that for the B epitope arrayed alone was 616 copies\dextran molecule. Groups of Balb\c female mice (n=8) were injected ip with either 45 ug of the co-array [(B+T)-dex$_{500}$] or with 100 ug of the B epitope conjugated to dex$_{500}$ (B-dex$_{500}$) alone. Both types of construct were administered in PBS with or without 1 mg Al(OH)$_3$ as adjuvant.

Nineteen days later mice received a second dose of 100 ug of the same construct. In all cases, doses were based on the weight of the dextran. Sera were obtained pre-boost and fourteen days post-boost and were assayed for the presence of IgG anti-B epitope antibodies by ELISA using gelatin conjugated with the HIV peptide to coat the plates.

In mice receiving B-dex$_{500}$, no IgM nor IgG antibody response was seen. However, the co-array induced an IgG antibody response after a second injection (FIG. 9). Adjuvant, however, was required in this instance. This peptide had a short half-life of 0.64 hr in murine plasma and thus the presence of adjuvant probably protects this epitope from degradation.

Example 9

Inherent Immunogenicity

The following illustrates that inherent immunogenicity of the current constructs is critical. An IgG anti-Fl antibody response was established in Balb\c mice by injection of Fl coupled to cOA in adjuvant. Mice were then treated with a co-array consisting of dextran of 70,000 Da molecular weight (dex$_{70}$) conjugated with Fl and the T cell epitope, cOA 323–339. According to the Immunon hypothesis, this construct is sub-threshold and should be inhibitory rather than stimulatory.

Balb\c female mice were given two injections two months apart of 10 ug Fl-OA on 1 mg Al(OH)$_3$ to establish an IgG anti-Fl antibody response. Seventeen days after the second injection, the mice were divided into groups of 8 and were either injected with PBS, with 4 mg (Fl+peptide)-dex$_{70}$ or with 2 mg Fl-dex$_{70}$. Sera were obtained pre-treatment and at various times thereafter and were subsequently assayed by ELISA for the presence of IgG anti-Fl antibodies using gelatin conjugated with Fl at a low substitution density to coat the plates.

As shown in FIG. 10, this co-array does indeed induce chronic suppression of the anti-Fl response. However, the response first shows an immediate reduction followed by a recovery before the attainment of the chronically suppressed state. In contrast, the construct consisting of only Fl on dex$_{70}$ induced chronic suppression without displaying the preliminary "bouncing" of the antibody levels. Thus, even in the presence of a potent T cell epitope, a construct consisting of dextran of sub-threshold size becomes suppressive presumably because the T epitope is metabolized from the backbone and thus no T cell signals are available to "rescue" the B cells from suppression. (There are examples of this "rescue" in the literature e.g., Cooke, M. P., A. W. Heath, K. M. Shokat, Y. Zeng, F. D. Finkelman, P. S. Linsley, M. Howard and C. C. Goodnow (1994) J. Exp. Med. 179:425).

REFERENCES CITED

Dintzis, et al., *J. Immunol.* 143:1239 (1989).
Harada et al., *Experientia* 41:1584 (1985).
Shimonkevitz et al., *J. Immunol.* 133:2067 (1984).
Snapper et al., *J. Exp. Med.* 175:1367 (1992).
Dame et al., *Science* 225:593 (1984).
Eichinger et al., Mol.Cell.Biol. 6:3965 (1986).
Rusche et al., *Proc.Natl.Acad.Sci. USA* 85:3198 (1988).
Takahashi et al., *J. Exp. Med.* 171:571
Panina-Bordignon et al., *J. Immunol.* 19:2237 (1989).
Barany, et al., *The Peptides: Analysis, Synthesis, Biology;* Gross, E., Meienhofer, J., Eds.; Academic Press: New York, Vol.2; pp 1–284 (1980).
Stewart, et al., Laboratory Techniques in Solid-Phase Peptide Synthesis. In *Solid-Phase Peptide Synthesis,* 2nd ed.; Pierce Chemical Company: Rockford, Ill., pp 85–88 (1984).
Bidlingmeyer, et al., *J. Chromatogr.* 336:93–104 (1984).

What is claimed is:

1. A construct capable of inducing IgG, IgA, or IgE antibodies to a B-cell epitope comprising:

a carrier having a molecular weight of at least about 100 KDa;

at least about 20 copies of said B-cell epitope attached to said carrier; and at least one copy of a T-cell epitope, said T-cell epitope being separate and distinct from said B-cell epitope, attached to said carrier at a site distinct from the attachment site of said B-cell epitope.

2. The construct according to claim 1, wherein the construct is capable of inducing IgG antibodies to said B-cell epitope or epitopes.

3. The construct according to claim 1, wherein the B-cell epitope is an epitope derived from HIV.

4. The construct according to claim 1, wherein the B-cell epitope is an epitope derived from human malaria parasites.

5. The construct according to claim 1, wherein the T-cell epitope is a tetanus toxoid, PPD or malaria CS.T3.

6. The construct according to claim 1, wherein said construct is capable of inducing IgG, IgA or IgE antibodies to more than one B-cell epitope, said construct comprising at least about 20 copies of each B-cell epitope.

7. The construct according to claim 1, wherein said construct further comprises at least two different T-cell epitopes.

8. A method of eliciting an IgG response to a B-cell epitope in a host comprising administering an immunogenic amount of the construct according to claim 1.

9. A method of assessing whether a moiety functions as a T-cell epitope, comprising:

attaching at least about 20 copies of a B-cell epitope to a carrier, said carrier having a molecular weight of at least about 100 KDa;

attaching one or more copies of said moiety to said carrier at a site distinct from the attachment site of said B-cell epitope, said moiety being separate and distinct from said B-cell epitope;

administering the resulting construct to a host; and assaying a blood sample from said host for the presence of anti-B-cell epitope IgG, IgA or IgE antibodies in a primary response and in response to a secondary challenge with said construct.

10. A method of assessing whether a moiety functions as a B-cell epitope, comprising:

attaching at least one copy of a T-cell epitope to a carrier, said carrier having a molecular weight of at least about 100 KDa;

attaching at least about 20 copies of said moiety to said carrier at a site distinct from the attachment site of said T-cell epitope, said moieties being separate and distinct from said T-cell epitope;

administering the resulting construct to a host; and assaying a blood sample from said host for the presence of anti-moiety IgG, IgA or IgE antibodies.

* * * * *